United States Patent
Zemp (10) Patent No.: US 10,228,339 B2
(45) Date of Patent: Mar. 12, 2019

(54) DETECTING CONDUCTORS IN A CABLE-STRIPPING PROCESS

(71) Applicant: Komax Holding AG, Dierikon (CH)

(72) Inventor: Benno Zemp, Eschenbach (CH)

(73) Assignee: KOMAX HOLDING AG, Dierikon (CH)

( * ) Notice: Subject to any disclaimer, the term of this patent is extended or adjusted under 35 U.S.C. 154(b) by 219 days.

(21) Appl. No.: 14/436,497

(22) PCT Filed: Oct. 3, 2013

(86) PCT No.: PCT/EP2013/070640
§ 371 (c)(1),
(2) Date: Apr. 17, 2015

(87) PCT Pub. No.: WO2014/060218
PCT Pub. Date: Apr. 24, 2014

(65) Prior Publication Data
US 2015/0300971 A1 Oct. 22, 2015

(30) Foreign Application Priority Data
Oct. 18, 2012 (EP) .................................. 12189012

(51) Int. Cl.
G01N 27/22 (2006.01)
H01R 43/28 (2006.01)
H02G 1/12 (2006.01)

(52) U.S. Cl.
CPC ............ *G01N 27/22* (2013.01); *H01R 43/28* (2013.01); *H02G 1/1202* (2013.01); *H02G 1/1209* (2013.01); *H02G 1/1253* (2013.01)

(58) Field of Classification Search
CPC .. H02G 1/1202; H02G 1/1253; H02G 1/1209; G01N 27/22; H01R 43/28
(Continued)

(56) References Cited

U.S. PATENT DOCUMENTS

2007/0121796 A1   5/2007  Lurati et al.
2010/0181180 A1*  7/2010  Peter .................... H03K 17/955
                                                          200/5 R
2010/0251857 A1* 10/2010  Whittaker ............. H01R 43/05
                                                          81/9.4

FOREIGN PATENT DOCUMENTS

DE   102007053825 A1   5/2009
DE   102009027967 A1   2/2010
(Continued)

*Primary Examiner* — Melissa Koval
*Assistant Examiner* — Courtney McDonnough
(74) *Attorney, Agent, or Firm* — William J. Clemens; Shumaker, Loop & Kendrick, LLP (57) ABSTRACT

While stripping an electrical cable in a stripping device of a cable-processing system, detection by an electrically conductive cutting device with a sensor circuit takes place if contact with a conductor occurs. By connecting the sensor circuit to the cutting device a measuring capacitance is developed. Before incising the electrical cable, a capacitance value of the measurement capacitance is determined during a first measurement cycle in which a charge equalization is carried out between the measurement capacitance and a reference capacitance. A parameter is determined in a further measurement cycle in which a charge equalization is again carried out between the measurement capacitance and the reference capacitance, wherein, relative to the first capacitance, the parameter displays a change in the capacitance after incising into the electrical cable. A signal is produced, if the change is greater than an established threshold value, indicating contact with the conductor.

16 Claims, 3 Drawing Sheets

(58) Field of Classification Search
USPC .......................................................... 324/663
See application file for complete search history.

(56) References Cited

FOREIGN PATENT DOCUMENTS

| | | |
|---|---|---|
| JP | H02106108 A | 4/1990 |
| JP | H0646657 A | 2/1994 |
| JP | H06253430 A | 9/1994 |
| JP | H07236214 A | 9/1995 |
| JP | 2777022 B2 | 7/1998 |
| JP | H11299036 | 10/1999 |
| JP | 2000354315 A | 12/2000 |
| WO | 2012015062 A1 | 2/2012 |

\* cited by examiner

Fig. 2

DETECTING CONDUCTORS IN A CABLE-STRIPPING PROCESS

FIELD

The embodiments described here relate generally to an installation for processing electric cables. These embodiments relate to, in particular, stripping an electric cable.

BACKGROUND

A known electric cable has an electrically conductive (inner) conductor and an insulating sheathing of plastics material, which encloses the conductor along its length and electrically insulates it. The conductor can be a wire or a strand. In order to connect the electric cable with different electrical components (for example plugs, terminals) a part of the insulating sheathing can be removed at a cable end so that the bare conductor is exposed. The process of removal of the insulating sheathing is also termed stripping.

Industrial stripping of electric cables is usually carried out in a cable processing installation which is specially provided for that purpose and in which a knife of a stripping device initially cuts through the insulating sheathing in the region of a cable end and then pulls off the conductor the piece of insulating sheathing to be separated. During the stripping process the conductor of the electrical cable should not, if possible, be contacted or damaged by the knife.

Due to constantly increasing demands on quality in the mechanically executed stripping process it is necessary to monitor the stripping process. In that case it should be reliably detected whether a conductor of such an electric cable is damaged during this stripping process. Damage can consist of the conductor being cut into by the knife or even severed.

DE-A-10200753825 shows a stripping device for electric cables, which device comprises a capacitive sensor unit and an electrically conductive knife. The capacitive sensor unit is connected with the knife and constructed in such a way that contact of the conductive knife with a conductor of the cable can be detected on the basis of an increase in capacitance. The sensor unit comprises an alternating voltage generator which produces a sine signal. An internal resistance of the alternating voltage generator forms, together with the measured capacitance, a voltage divider so that the sensor unit can detect conductor contact on the basis of a reduction in the voltage amplitude of the sine signal. Such a stripping device has the disadvantage that contact detection on the basis of the sine signal can take place only slowly.

SUMMARY

It is therefore an object of the invention to provide improved technology for stripping an electric cable, which enables more rapid detection of contact of the knife with the conductor.

One aspect therefore relates to a method for detecting contact of a conductor of an electric cable by an electrically conductive knife during a stripping process in a stripping device of a cable processing installation, wherein a sensor circuit is connected with the knife by way of a connection so that a measuring capacitance forms. The method comprises determination of a first capacitance value of the measuring capacitance during a first measuring cycle, in which charge equalization between the measuring capacitance and a reference capacitance is carried out, wherein the first capacitance value is determined prior to cutting into the electric cable. The method additionally comprises determination of a parameter in a further measuring cycle in which charge equalization between the measuring capacitance and the reference capacitance is carried out again, wherein the parameter referred to the first capacitance value indicates a change in a capacitance value of the measuring capacitance after the electric cable has been cut into. The method further comprises generating a signal if the change is greater than a fixed threshold value, in which case the signal indicates contact with the conductor.

It can be advantageous if during the stripping process a plurality of further measuring cycles, preferably a fixed number of further measuring cycles, is carried out. In that case, in each of the further measuring cycles determination of the parameter is referred to the first capacitance value from the first measuring cycle. Due to the fact that for the further measuring cycles the first capacitance value from the first measuring cycle forms the reference variable a higher level of sensitivity can be achieved. Erroneous detections (for example, fault reports just on contacting the insulation) can thus be virtually excluded.

A further aspect relates to a cable processing device with a stripping device for carrying out the stated method.

The improved technology, which is described here, for stripping an electric cable is based on a charge equalization which takes place between electrical components when these are connected together. In one embodiment, in this method at the start an unknown capacitance is discharged and a known capacitance is charged, so that a defined voltage is present thereat. Thereafter, the known and unknown capacitances are connected in parallel so that a charge equalization can take place. After the charge equalization there is present at the parallel circuit of known and unknown capacitances a smaller voltage than before, which is measured. The defined voltage and the measured voltage are used for the purpose of ascertaining contact of a knife with the conductor or an immediate proximity of the knife to the conductor. Determination of contact takes place by means of, for example, calculation of a value of the unknown capacitance. If the measuring cycles are repeated it can thus be established when this value changes and thus indicates conductor contact.

In one embodiment it can be fixed how many further measuring cycles are carried out during the stripping process. Since in each of these measuring cycles a statement about the value of the measuring capacitance is made, it is possible to achieve a high level of resolution along the stripped conductor if a high number of further measuring cycles is fixed.

In the embodiments described here the first capacitance value, which is determined in the first measuring cycle, is a measure for the purpose of being able to make, in further measuring cycles, statements about whether the capacitance value of the measuring capacitance has changed relative to the first capacitance value, for example because a knife has contacted the conductor. The first capacitance value is determined again prior to each stripping process.

In one embodiment the first measuring cycle comprises producing a defined voltage state at the measuring capacitance and charging of the reference capacitance, so that a first voltage with a first voltage value is present at the capacitance circuit. Thereafter, an electrical connection between the measuring capacitance and the reference capacitance is produced so as to enable charge equalization between the measuring capacitance and the reference capacitance. A second voltage, which is present at the reference capacitance after the charge equalization and which has a second voltage value, is measured and the first capacitance value of the measuring capacitance is determined by means of the voltage values and the reference capacitance.

Production of the defined voltage state can take place in different ways. In one case, the measuring capacitance can be short-circuited and in a further case a defined voltage potential can be coupled to the measuring capacitance. The technology described here can thus be flexibly adapted to different conditions with respect to the reference potential of the cable processing installation.

The statement about the value of the measuring capacitance can be effected by means of different parameters depending on the respective embodiment. In one embodiment the parameter is a second capacitance value of the measuring capacitance, wherein the signal is generated when the difference between the first capacitance value and the second capacitance value exceeds the fixed threshold value. In this embodiment an absolute capacitance value, the change in which can be monitored, is present after each further measuring cycle.

In another embodiment the absolute capacitance value of the measuring capacitance is not relevant. It is therefore possible to dispense with calculation thereof, whereby computing cost in a control unit is reduced. Instead, change in the capacitance value is indirectly monitored in that there is monitored as parameter merely a voltage which can be measured at the reference capacitance after charge equalization, whilst the measuring capacitance is connected in parallel therewith.

In a further embodiment the components of the sensor circuit are so selected that after each charging process substantially the same voltage arises at the reference capacitance. It is thus sufficient for this voltage to be measured only once; it is possible to dispense with measurements of this voltage in subsequent measuring cycles. A further reduction in measuring effort thereby arises.

If, moreover, in the afore-mentioned embodiment only a statement about a change in the capacitance value is relevant and not a statement about the absolute value thereof, it is possible to entirely dispense with measurement of the voltage at the reference capacitance after a charging process. Instead of a measured voltage value, use can be made for that purpose of a constant.

The speed of this method is dependent on switches, the settings of which are changed in the course of the method, on the speed of the charging or discharging of individual elements of the stripping device participating in this method and on the speed of the voltage measurement. The switches are preferably low-maintenance analog switches with short switching times. The switches are controlled by a control unit inter alia so that all switches are opened before a switching process is carried out.

In a development of the method the knife is readjusted in the case of occurrence of the signal, wherein a spacing of the knife from a longitudinal axis of the electric cable is changed. As a result of increase in the spacing of the knife from the longitudinal axis it can be ensured that the knife does not damage or further contact the conductor in the further course of the stripping process.

In a development of the method the signal produces a warning tone and/or stopping of the stripping process and/or deposit of the electric cable in a special deposit and/or inclusion in a statistical evaluation. Depending on the respective interpretation of the signal different possibilities of continuing the stripping process of the electric cable can be selected after occurrence of such a signal. For example, the attention of the person supervising the stripping process can be accordingly drawn to a need for recalibration of the stripping device. For example, the signal can equally be interpreted in such a way that the electric cable is damaged and accordingly cannot be reused.

It is also an advantage of the technology described here that it can be used not only in different cable processing installations (for example, installations for cutting cables to length and for stripping, and installations with several different functions and process steps), but also in simple stripping pliers.

DESCRIPTION OF THE DRAWINGS

Different embodiments of the improved technology for detection of conductor contact are described in detail in the following on the basis of the accompanying drawings, in which the same components have the same reference numerals and in which.

DETAILED DESCRIPTION

Figure 1:
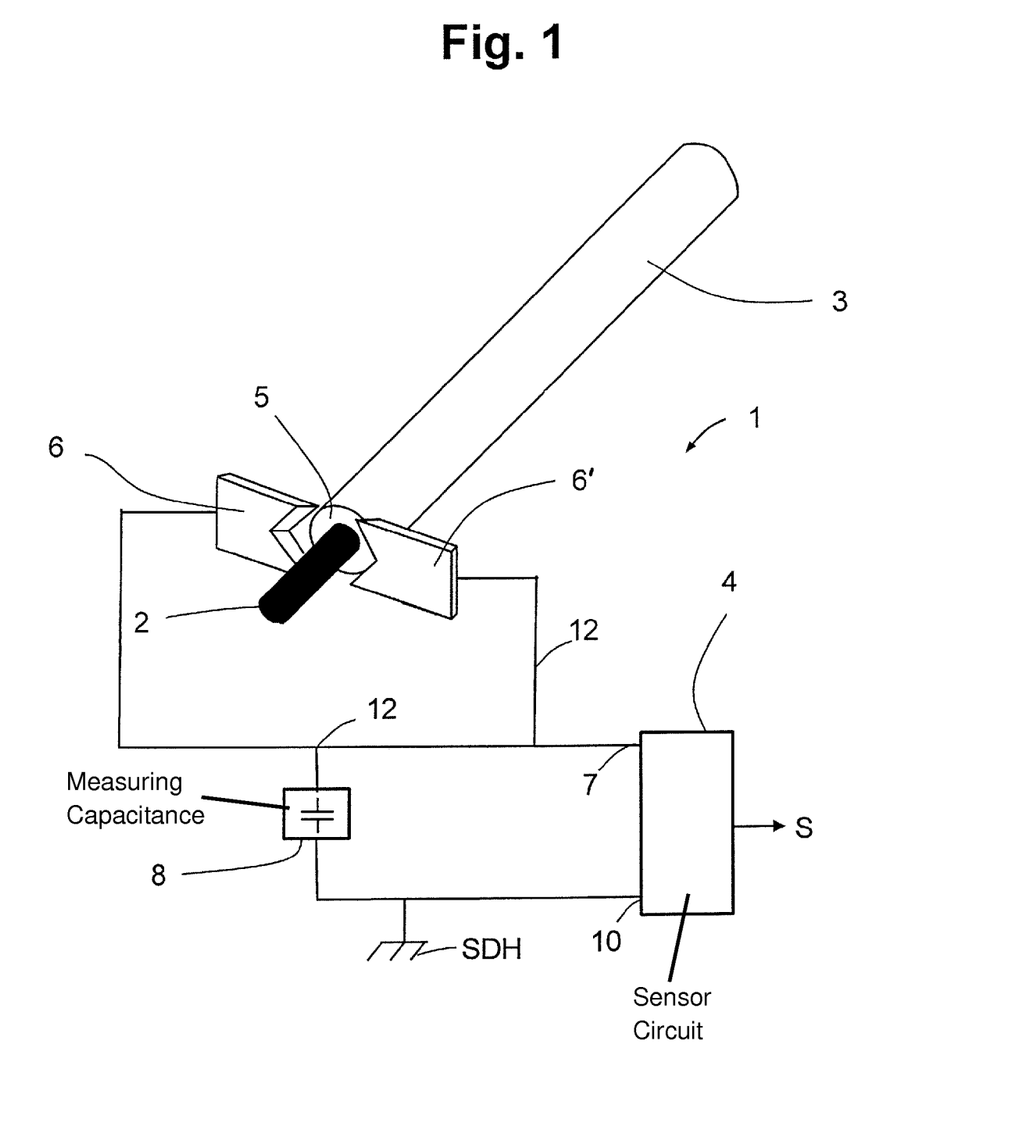
FIG. 1 shows a simplified schematic illustration of a cable processing installation with an embodiment of a stripping device with a sensor circuit.

FIG. 1 shows a simplified schematic illustration of a cable processing installation with an embodiment of an insulating device 1, which comprises a sensor circuit 4. The installation processes an electric cable 3, which has an electrically conductive (inner) conductor 2 and an insulating sheathing 5 of plastics material, which encloses the conductor 2 along the length thereof and electrically insulates it. The conductor 2 can be a wire or a strand. For the sake of clarity, further parts of the cable processing installation are not shown in FIG. 1. However, the expert will recognize that an example of a known cable processing installation, for example a Kappa 330 of the company Komax AG, Switzerland, comprises a central control, an operating device and modules for additional functions such as, for example, cutting to length.

A function of the stripping device 1 is described in more detail in the following on the basis of an embodiment. This function relates to determining whether a cutting device has contacted the conductor 2 during the stripping, so as to be able to thereby assess the quality of the stripped conductor 2. As shown in FIG. 1, the cutting device in one embodiment of the stripping device 1 consists of two oppositely arranged electrically conductive knives 6, 6'. A control device, which is not shown in FIG. 1, controls the knives 6, 6' in order to move these in the direction of the electric cable 3 for the purpose of closing or away from this for the purpose of opening. Similarly not shown are a mount for the electric cable 3 and one or more drive devices (for example, for advance of the electric cable 3) in order to move the knives 6, 6' and the electric cable 3 relative to one another. The stripping device 1 controls, by mechanical action, the relative movements between the electric cable 3 and the knives 6, 6'.

The sensor circuit 4 shown in FIG. 1 is connected by way of a first connection 7 with the knives 6, 6' and by way of a second connection 10 with a defined potential. The respective connections can be effected by means of one or more connecting lines 12. In FIG. 1, the connecting lines 12 are arranged outside the sensor circuit 4. However, the expert will recognize that the connecting lines 12 can also be associated with the sensor circuit 4. The sensor circuit 4 can be constructed from, for example, discrete electronic components. The sensor circuit thus does not necessarily have to be constructed as an integrated circuit, whereby the circuit can be produced economically at low cost. A sensor circuit assembled in that way from discrete electronic components allows selection of further suitable components (such as, for example, fast-action switches) and thus optimization in simple manner of the sensor circuit with respect to electromagnetic compatibility.

The defined potential is the reference potential for all signalling and operating voltages of the stripping device 1 or the cable processing plant. The reference voltage can be 0 volts (i.e. there is earthing) or a different potential. A general short designation for this reference potential is SHD, which stands as an abbreviation for the English term "shielding". In the following, the reference potential is termed reference potential SHD.

FIG. 1 additionally shows a measuring capacitance 8, which is illustrated by the usual symbol for a capacitor. In this symbolic illustration the measuring capacitance 8 is present between the first connection and the second connection, which is connected with the reference potential SHD, of the sensor circuit 4. This measuring capacitance 8 is an equivalent circuit for a plurality of capacitances and thus represents a sum of capacitances which exist as (parasitic) capacitances with respect to the reference potential SHD when the sensor circuit 4 is connected with the knives 6, 6'. The measuring capacitance 8 therefore comprises the capacitances which arise primarily due to the connecting lines 12, the knives 6, 6' and parts of the sensor circuit 4. In the embodiments described here, the measuring capacitance 8 is, in the mathematical sense, an unknown which is determined with the help of measured voltage values.

The knives 6, 6' are mounted in the stripping device 1 to be electrically insulated, i.e. there is no electrical connection between the knives 6, 6' and the reference potential SHD.

If there is contact of the knives 6, 6' with the conductor 2 the measuring capacitance 8 changes, since in this case the capacitance present between the conductor 2 and the reference potential SHD is added. The sensor circuit 4 operates according to the principle of capacitive charge equalization and determines, in one embodiment, a value for the capacitance by means of voltage measurements per measuring cycle. If the sensor circuit 4 ascertains increase in the capacitance, it derives therefrom the fact that at least one of the knives 6, 6' has contacted the conductor 2 and it generates a signal S as described in more detail in the following. The signal S can be processed by means of a superordinate control unit of the stripping device 1 so as to appropriately influence the further course of the stripping process.

Figure 2:
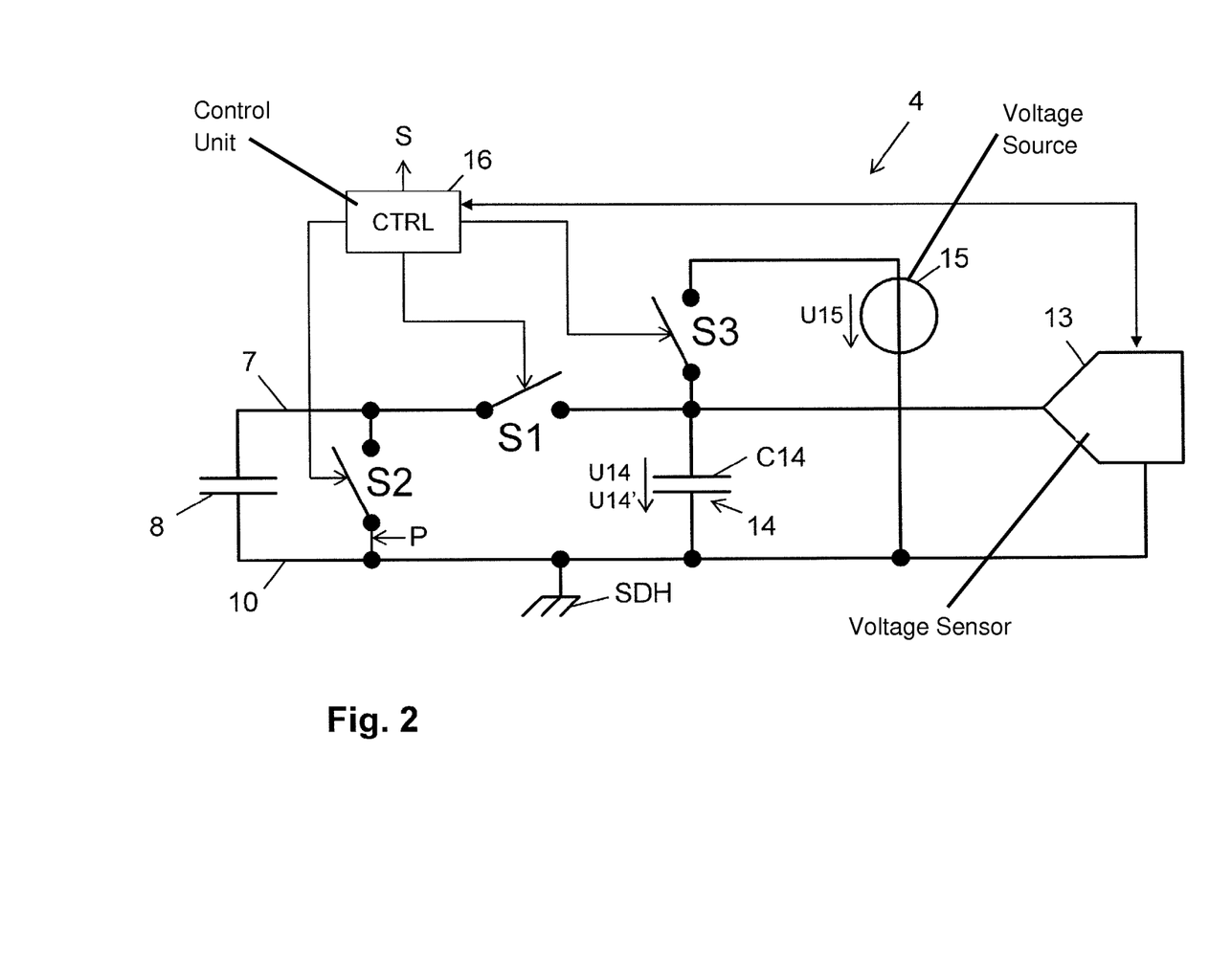
FIG. 2 shows a simplified circuit diagram of an embodiment of the sensor circuit.

FIG. 2 shows a simplified schematic diagram of an embodiment of the sensor circuit 4, which according to FIG. 1 is connected with the knives 6, 6'. The measuring capacitance 8, which as described represents—as an equivalent circuit—the sum of several (parasitic) capacitances is for better understanding shown in FIG. 2 as connected with the sensor circuit 4. The connection is effected by way of connections 7, 10 of the sensor circuit 4, in which case parasitic capacitances of the sensor circuit 4 are themselves equally counted as the measuring capacitance 8. The sensor circuit 4 comprises switches S1, S2, S3, a capacitance circuit 14 with a reference capacitance C14 and possibly further parasitic capacitances caused by feed lines (in the following reference is made only to the reference capacitance C14), a voltage sensor 13, a control unit 16 and a voltage source 15. The voltage source 15 supplies a voltage U15. The control unit 16 is connected with the switches S1, S2, S3 in order to selectively activate these so that the switches S1, S2, S3 are either open or closed. In FIG. 2, the switches S1, S2, S3 are open.

The basic arrangement of these components of the sensor circuit 4 is as follows: The switch S2 is connected in parallel with the connections 7, 10 and is thus also connected in parallel with the measuring capacitance 8, wherein the connection 10, a connection of the switch S1 and a connection of the reference capacitance C14 are connected with the reference potential SHD. If the switch S1 is closed, the reference capacitance C14 is connected in parallel with the switch S2; if the switch S1 is open, the reference capacitance C14 is separated from the switch S2. The voltage sensor 13 is connected in parallel with the reference capacitance C14; if the switch S1 is closed and the switch S2 open, the voltage sensor 13 is also connected in parallel with the measuring capacitance 8. The voltage source 15 is connected in parallel with the reference capacitance C14 when the switch S3 is closed and is separated therefrom when the switch S3 is open.

In one embodiment the voltage sensor 13 includes an analog-to-digital converter which in known manner converts an analog input signal into a digital output signal. In the sensor circuit 4 described here the analog input signal is an analog voltage value which is, for example, present at the input of the voltage sensor 13 at a specific point in time. The voltage sensor 13 converts this analog voltage value into a digital voltage value which the control unit 16, which is connected with an output of the voltage sensor 13, further processes. The control unit 16 can so control the voltage sensor 13 that a voltage conversion is performed only at specific points in time. Alternatively thereto the voltage sensor 13 can be designed so that it continuously converts the input voltage, but the control unit 16 'interrogates' the output voltage only at specific points in time in order to then subject it to further processing.

The control unit 16, the voltage sensor 13 and the switches S1, S2, S3 are constructed so as to do justice to demands on the speed of monitoring or regulation of the stripping process. In an embodiment, it is established in the control unit 16 within which time a measuring cycle takes place and how often this measuring cycle is repeated. In correspondence with this determination the control unit 16 activates the switches S1, S2, S3 and the voltage sensor 13. For the switches S1, S2, S3 this means, for example, that they can open and close sufficiently rapidly. In an embodiment, the switches S1, S2, S3 are executed as integrated circuits or analog switches (for example, based on field effect transistors). However, also any other kind of switching means is usable insofar as it can open and close an electrical line connection with appropriate rapidity.

If integrated circuits are used for the switches S1, S2, S3, up to 250,000 measuring cycles per second can be performed. This enables a far and away more rapid detection or processing of contact of the knives 6, 6' with the conductor 2 than is the case with the system known from DE-A-102007053825.

FIG. 2 additionally shows a point P between the switch S2 and the reference potential SHD. In one embodiment a voltage source can be added at this point in order to pre-charge the measuring capacitance 8 to a potential, which is predetermined by this voltage source, when the switch S2 is closed and the switch S1 open.

Figure 3:
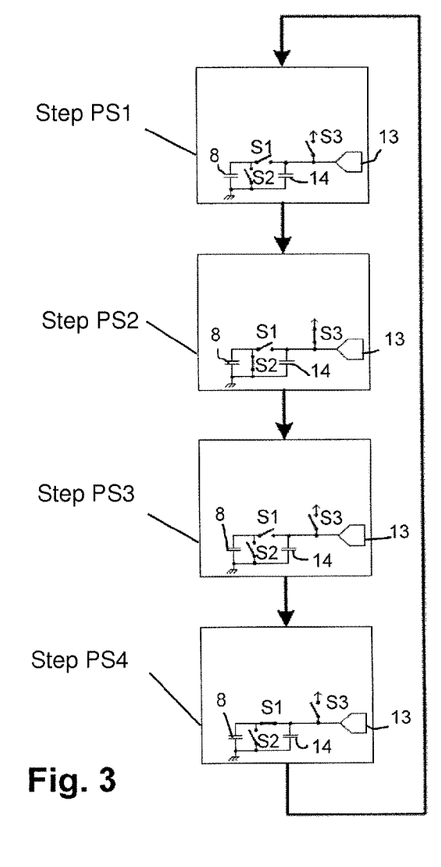
FIG. 3 shows a simplified and exemplifying illustration of a measuring cycle.

The functioning of the sensor circuit is described in the following with reference to FIG. 2 and FIG. 3, which show an embodiment of a measuring cycle with four process steps PS1 to PS4. In these process steps PS1 to PS4, for the sake of better clarity only the measuring capacitance 8 and some of the components of the sensor circuit 4 are shown. A measuring cycle begins with application of the knives 6, 6', but without in that case cutting into the insulating sheathing 5, and ends when the knives 6, 6' have reached the cable end, from which the piece of insulating sheathing 5 is pulled off and the conductor 2 is bared.

In the process steps PS1 and PS3 all switches S1, S2, S3 are open. These process steps PS1 and PS3 serve, in the illustrated embodiment, for preparation for succeeding process steps. These steps ensure that the switches S1, S2, S3 are each in a defined setting of 'open' before further switching processes are carried out. This prevents occurrence of short-circuits. However, the expert will recognize that these preparatory steps can also be omitted if the risk of possible short-circuits has been eliminated in another way, for example by precise synchronization of the switching processes or by defined waiting times.

In process step PS2 the switches S2, S3 are closed and the switch S1 is open. The closed switch S2 short-circuits the measuring capacitance 8, whereby the measuring capacitance 8 is discharged; the voltage at the measuring capacitance 8 is 0 volts. The measuring capacitance 8 thus has a defined state (charge Q equal to zero, voltage equal to 0 volts).

The closed switch S3 connects the voltage source 15 with the reference capacitance C14, whereby the reference capacitance C14 is charged. After charging, a voltage U14 at the reference capacitance C14 corresponds with the voltage U15 predetermined by the voltage source 15. In one embodiment, the predetermined voltage U15 is less than 5 volts. The reference capacitance C14 thus has a defined state (voltage U14 equal to predetermined voltage U15, charge Q equal to the product of voltage U14 and capacitance of the reference capacitance C14).

The switch S3 can then be opened by the control unit 16. Since the switch S1 is open, ideally no charge flows away from the reference capacitance C14 and it remains in its defined state. The voltage U14 is then measured at the reference capacitance C14 by the voltage sensor 13. The voltage U14 measured in this state is stored, either in the voltage sensor 13 or in the control unit 16.

After all switches S1, S2, S3 have been opened again in process step PS3, in process step PS4 only the switch S1 is closed by the control unit 16. The measuring capacitance 8 and the reference capacitance C14 are thereby connected in parallel. Charge thereby flows from the reference capacitance C14 to the measuring capacitance 8 until the charges on both capacitances have equalized. Such a charge equalization has an exponential course which depends on the participating capacitances and a series resistance (for example line resistance); it can, for example, be regarded as concluded after a few nanoseconds. One consequence of this charge equalization is that the voltage at the parallel circuit of measuring capacitance 8 and reference capacitance C14 drops. After charge equalization has ended, a reduced voltage U14' is measured by the voltage sensor 13. The voltage U14' measured in this state can be processed by the control unit 16 with the stored voltage U14 from the process step PS2.

The processing can in one embodiment consist of the control unit 16 determining, in each measuring cycle, an actual value C8 of the measuring capacitance 8. This value results from: $C8=C14*(U14/U14'-1)$.

If the value C8 of the measuring capacitance 8 is determined in each measuring cycle it can be ascertained after each measuring cycle whether the value C8 of the measuring capacitance 8 has changed. Since the value C8 of the measuring capacitance 8 during the stripping process can be determined frequently a high level of resolution along the stripped conductor 2 can be achieved.

In order to obtain a measure with regard to whether the value C8 of the measuring capacitance 8 increases during the stripping process the value C8 of the measuring capacitance 8 is determined at the start of each stripping process with the knives 6, 6' open and shortly before cutting into the insulating sheathing 5. This (first) value C8 of the measuring capacitance 8 represents a reference value and means 'conductor not contacted'. In one embodiment, the control unit 16 stores the reference value.

Thereafter, the knives 6, 6' are closed and cut into the insulating sheathing 5 and in a further measuring cycle, in which a charge equalization between the measuring capacitance 8 and the reference capacitance C14 is carried out again, a parameter is determined which, referred to the first capacitance value, indicates a change in the capacitance value of the measuring capacitance 8 after cutting into the electric cable 3. In one embodiment, the value C8 of the measuring capacitance 8 is determined again in a further measuring cycle.

Even if the knives 6, 6' do not contact the conductor 2 the value C8 of the measuring capacitance 8 changes as a consequence of changing geometries while the knives 6, 6' cut through the insulating sheathing 5. In the case of suitable design, however, this change is not as strong as would be the case on contact with the conductor 2. In order not to falsely treat such a change in the value C8 of the measuring capacitance 8 as conductor contact a capacitance threshold value is fixed and stored in the control unit 16. If the difference of the reference value and a value C8, which is determined in a measuring cycle, of the measuring capacitance 8 exceeds the fixed capacitance threshold value this means 'conductor contacted' and the control unit 16 generates the signal S.

In one embodiment, a repetition frequency of the first voltage U14 can fulfil specified demands on accuracy. This means that if the reference capacitance C14 is repeatedly discharged and charged by the voltage source 15 the first voltage U14 present after each charging process has substantially the same voltage value. In such an embodiment it is possible to dispense with measurement of the first voltage U14 in each measuring cycle. The first voltage U14 is in this case measured only once and the determined voltage value is used again for all following measuring cycles.

In the embodiments described here, primarily the changes in the value C8 of the measuring capacitance 8 are of interest for the evaluation; an absolute value of the value C8 of the measuring capacitance 8 can thus be irrelevant depending on the embodiment. In the case of sufficient repetition accuracy of the first voltage U14 it is possible in such examples of use to entirely dispense with determination of the first voltage U14 and instead to make use of a fixed constant.

If in a further embodiment the absolute value of the value C8 of the capacitance 8 is irrelevant, then the change therein can be indirectly monitored in that merely the second voltage U14' is monitored. The voltage U14' serves as a parameter in order to indicate, with reference to the first capacitance value, a change in the capacitance value C8 of the measuring capacitance 8 after cutting into the electric cable 3. The capacitance value itself is not calculated in this case. The signal S is generated when a difference between the second voltage value of the first measuring cycle and the second voltage value of the further measuring cycle exceeds a fixed voltage threshold value.

A superordinate control unit of the cable processing installation receives the signal S and triggers a procedure usual for electric cable produced with inadequate quality. This procedure can comprise issue of a warning tone, stopping of production or rejecting such electric cable as waste. In addition, the signal S can be used for readjusting a spacing of the knives 6, 6' from a longitudinal axis of the electrical cable 3 to be stripped.

In accordance with the provisions of the patent statutes, the present invention has been described in what is considered to represent its preferred embodiment. However, it should be noted that the invention can be practiced otherwise than as specifically illustrated and described without departing from its spirit or scope.

The invention claimed is:

1. A method for detecting contact of a conductor of an electric cable by an electrically conductive knife during a stripping process in a stripping device of a cable processing installation, wherein a sensor circuit is connected with the knife by a connection forming a measuring capacitance, the method comprising the steps of:
prior to cutting into the electric cable with the knife, determining a first capacitance value of the measuring capacitance during a first measuring cycle in which charge equalization between the measuring capacitance and a reference capacitance of a capacitance circuit of the sensor circuit is performed;
determining a parameter in a further measuring cycle in which charge equalization between the measuring capacitance and the reference capacitance is performed again, wherein the parameter indicates a change in a capacitance value of the measuring capacitance after the electric cable has been cut into by the knife; and
generating a signal if the change is greater than a fixed threshold value, wherein the signal indicates contact with the conductor by the knife;
wherein the first measuring cycle includes the following steps:
producing a defined voltage state at the measuring capacitance;
charging the reference capacitance so that a first voltage with a first voltage value is present at the capacitance circuit;
producing an electrical connection between the measuring capacitance and the reference capacitance enabling charge equalization between the measuring capacitance and the reference capacitance;
measuring a second voltage which is present at the reference capacitance after the charge equalization and which has a second voltage value; and
determining the first capacitance value of the measuring capacitance from the first and second voltage values and the reference capacitance;
including a further measuring cycle with the following steps:
producing the defined voltage state at the measuring capacitance;
charging the reference capacitance so that the first voltage is present at the capacitance circuit;
producing the electrical connection between the measuring capacitance and the reference capacitance enabling charge equalization between the measuring capacitance and the reference capacitance;
measuring the second voltage which is present at the reference capacitance after the charge equalization and which has the second voltage value; and
determining the parameter;
and wherein the first voltage value is measured in the first measuring cycle and is used in a further measuring cycle, and producing the defined voltage state includes coupling a defined voltage potential to the measuring capacitance.

2. The method according to claim 1 wherein during the stripping process a fixed number of further measuring cycles is carried out and wherein in each of the further measuring cycles determination of the parameter is referred to the first capacitance value from the first measuring cycle.

3. The method according to claim 1 wherein the first voltage value has a substantially constant value.

4. The method according to claim 1 wherein the parameter is a second capacitance value of the measuring capacitance and wherein the signal is generated when a difference between the first capacitance value and the second capacitance value exceeds a fixed capacitance threshold value.

5. The method according to claim 1 wherein the parameter is the second voltage value and wherein the signal is generated when a difference between the second voltage value of the first measuring cycle and the second voltage value of the further measuring cycle exceeds a fixed voltage threshold value.

6. The method according to claim 1 wherein producing the defined voltage state includes short-circuiting the measuring capacitance.

7. The method according to claim 1 wherein producing the defined voltage state includes closing a second switch in parallel with the measuring capacitance when an open first switch separates the reference capacitance from the measuring capacitance.

8. The method according to claim 7 wherein charging the reference capacitance includes closing a third switch between the reference capacitance and a voltage source when the second switch is opened.

9. The method according to claim 8 wherein producing the electrical connection comprises closing the first switch, opening the second switch and opening the third switch.

10. The method according to claim 7 wherein all of the switches are opened before a switching process is carried out.

11. The method according to claim 1 wherein when the signal is generated the knife is readjusted and wherein a spacing of the knife from the electric cable containing the conductor is changed.

12. The method according to claim 1 including in response to the signal being generated performing at least one of generating a warning tone, stopping of the stripping process, depositing of the electric cable in a special deposit and performing a statistical analysis.

13. A cable processing insulating device with a stripping device for carrying out the method for detecting conductor contact by the electrically conductive knife in a stripping process according to claim 1.

14. The method according to claim 1 including a step of connecting a first connection of the sensor circuit to the knife and connecting a second connection of the sensing circuit to a reference potential whereby the measuring capacitance is a sum of all capacitances present between the first connection and the second connection.

15. A method for detecting contact of a conductor of an electric cable by an electrically conductive knife during a stripping process in a stripping device of a cable processing installation, wherein a sensor circuit is connected with the knife by a connection forming a measuring capacitance, the method comprising the steps of:
- prior to cutting into the electric cable with the knife, determining a first capacitance value of the measuring capacitance during a first measuring cycle in which charge equalization between the measuring capacitance and a reference capacitance of a capacitance circuit of the sensor circuit is performed;
- determining a parameter in a further measuring cycle in which charge equalization between the measuring capacitance and the reference capacitance is performed again, wherein the parameter indicates a change in a capacitance value of the measuring capacitance after the electric cable has been cut into by the knife;
- generating a signal if the change is greater than a fixed threshold value, wherein the signal indicates contact with the conductor by the knife;
- wherein the first measuring cycle includes the following steps:
  - producing a defined voltage state at the measuring capacitance;
  - charging the reference capacitance so that a first voltage with a first voltage value is present at the capacitance circuit;
  - producing an electrical connection between the measuring capacitance and the reference capacitance enabling charge equalization between the measuring capacitance and the reference capacitance;
  - measuring a second voltage which is present at the reference capacitance after the charge equalization and which has a second voltage value; and
  - determining the first capacitance value of the measuring capacitance from the first and second voltage values and the reference capacitance;
- including a further measuring cycle with the following steps:
  - producing the defined voltage state at the measuring capacitance;
  - charging the reference capacitance so that the first voltage is present at the capacitance circuit;
  - producing the electrical connection between the measuring capacitance and the reference capacitance enabling charge equalization between the measuring capacitance and the reference capacitance;
  - measuring the second voltage which is present at the reference capacitance after the charge equalization and which has the second voltage value; and
  - determining the parameter;
- and wherein the first voltage value is measured in the first measuring cycle and is used in a further measuring cycle.

16. A method for detecting contact of a conductor of an electric cable by an electrically conductive knife during a stripping process in a stripping device of a cable processing installation, wherein a sensor circuit is connected with the knife by a connection forming a measuring capacitance, the method comprising the steps of:
- prior to cutting into the electric cable with the knife, determining a first capacitance value of the measuring capacitance during a first measuring cycle in which charge equalization between the measuring capacitance and a reference capacitance of a capacitance circuit of the sensor circuit is performed;
- determining a parameter in a further measuring cycle in which charge equalization between the measuring capacitance and the reference capacitance is performed again, wherein the parameter indicates a change in a capacitance value of the measuring capacitance after the electric cable has been cut into by the knife;
- generating a signal if the change is greater than a fixed threshold value, wherein the signal indicates contact with the conductor by the knife;
- wherein the first measuring cycle includes the following steps:
  - producing a defined voltage state at the measuring capacitance;
  - charging the reference capacitance so that a first voltage with a first voltage value is present at the capacitance circuit;
  - producing an electrical connection between the measuring capacitance and the reference capacitance enabling charge equalization between the measuring capacitance and the reference capacitance;
  - measuring a second voltage which is present at the reference capacitance after the charge equalization and which has a second voltage value; and
  - determining the first capacitance value of the measuring capacitance from the first and second voltage values and the reference capacitance;
- and wherein the first voltage value is measured in the first measuring cycle and is used in a further measuring cycle, and producing the defined voltage state includes coupling a defined voltage potential to the measuring capacitance.

* * * * *